United States Patent [19]

Sherif

[11] Patent Number: 5,426,252
[45] Date of Patent: Jun. 20, 1995

[54] CATALYTIC HYDRODECHLORINATION OF A CHLOROMETHANE

[75] Inventor: Fawzy G. Sherif, Stony Point, N.Y.

[73] Assignee: Akzo Nobel nv, Arnhem, Netherlands

[21] Appl. No.: 138,291

[22] Filed: Oct. 15, 1993

[51] Int. Cl.$^6$ ..................... C07C 17/23; C07C 17/354
[52] U.S. Cl. ..................... 570/176; 570/101; 570/171; 570/257
[58] Field of Search ............... 570/176, 101, 240, 257

[56] References Cited

U.S. PATENT DOCUMENTS

| | | | |
|---|---|---|---|
| 3,579,596 | 5/1971 | Mullin et al. | 260/658 |
| 4,192,822 | 3/1980 | Sweeney et al. | 260/653 |
| 4,980,324 | 12/1990 | Kellner et al. | 502/36 |
| 5,057,470 | 10/1991 | Kellner | 502/35 |
| 5,094,988 | 3/1992 | Kellner et al. | 502/181 |
| 5,097,081 | 3/1992 | Correia et al. | 570/101 |
| 5,105,032 | 4/1992 | Holbrook et al. | 570/101 |
| 5,146,020 | 9/1992 | Rudershausen | 570/163 |
| 5,202,510 | 4/1993 | Kellner | 570/176 |

FOREIGN PATENT DOCUMENTS 319442  12/1989  Japan ..................... C07C 19/08

OTHER PUBLICATIONS

Journal of Catalysis 74, 136–143 (1982).
Inorganic Chemistry, vol. 31, No. 10, 1992, 1965–1968.
Catalysis Today, 15 (1992) 179–200.
A. M. Lovelace et al., Aliphatic Fluorine Compounds (ACS Monogram Series 1958), pp. 44–47, 92–93, 100–104, 133–136.
Fluorocarbons and Their Derivatives by R. E. Banks (MacDonald Technical & Scientific, 1970) pp. 17–18 and 65.
Journal of Catalysis 22, 245–254 (1971).

*Primary Examiner*—Howard T. Mars
*Attorney, Agent, or Firm*—Richard P. Fennelly; Louis A. Morris

[57] ABSTRACT

Chloromethane compounds including carbon tetrachloride and the chlorofluoromethane compounds, such as dichlorodifluoromethane, can be catalytically hydrodechlorinated, e.g., in the case of dichlorodifluoromethane to monochlorodifluoromethane and/or difluoromethane, by treatment with hydrogen in the presence of a transition metal carbide catalyst, for example, a Group IVB metal carbide, such as tungsten carbide, supported on an oxidic support, such as alumina, optionally with a passivating layer of ceramic, such as silicon carbide, between the oxidic support and catalyst. The catalyst preferably has a surface area of no less than about 1 $m^2/gm$.

10 Claims, No Drawings

CATALYTIC HYDRODECHLORINATION OF A CHLOROMETHANE

BACKGROUND OF THE INVENTION

The present invention relates to the catalytic hydrodechlorination of chloromethane compounds, e.g., carbon tetrachloride or chlorofluoromethanes, using a novel class of catalyst. The term "chloromethane" as used herein is intended to cover those methane compounds which have one or more of its hydrogen atoms substituted by chlorine, optionally also substituted by fluorine, and is capable of being catalytically hydrodechlorinated when reacted with hydrogen. It should also be understood that the present invention is useful with mixtures of such chloromethane compounds as well as compositions comprising only one such chloromethane compound.

For example, chlorofluorocarbons in the atmosphere are a matter of current concern regarding depletion of the ozone layer. Chlorofluorocarbons containing lower amounts of chlorine have been proposed as a substitute since the carbon-hydrogen bonds in such substitutes are more easily cleaned by chemical reactions at lower altitudes in the atmosphere than carbon-chlorine bonds thereby preventing the compound from reaching higher altitudes where ozone is present (see Inorganic Chemistry, Vol. 31, No. 10, 1992, pp. 1965-1968).

Noble metal catalysts, such as those containing palladium, have been proposed for use in the hydrodehalogenation of halogen-substituted hydrocarbons containing fluorine. Examples of U.S. patents relating to the use of this type of catalyst include: U.S. Pat. Nos. 4,980,324; 5,057,470; 5,094,988; and 5,202,510.

Transition metal carbide catalysts form a distinctly differing class of catalyst and have been proposed for use, in general, in a variety of processes including ammonia decomposition, hydrogenation and dehydrogenation, carbon monoxide methanation, isomerization, oxidation, hydrodesulfurization, and hydrodenitrogenation reactions. (see Catalysis Today, 15, 1992, pp. 179-200).

Tungsten carbide granules, which had been mixed with aluminum hydroxide to form a paste which was then spread onto an alumina honeycomb and heated at 500° C. to produce a catalyst, were also employed in the production of tetrafluoroethane from a haloethane containing four or five fluorine atoms, rather than in the treatment of a chlorofluoromethane compound. (See Japanese Patent Publication No. 01/319,442). Although the stability of saturated fluorocarbons exceeds that of their chlorocarbon analogues, the stability of the ethane-based fluorocarbons is less than that of the methane analogues (see R. E. Banks, Fluorocarbons and Their Derivatives, Macdonald Technical & Scientific, London, 1970, pp. 17-18).

In regard to the catalytic hydrodechlorination of carbon tetrachloride, platinum and palladium catalysts are described for use in U.S. Pat. No. 3,579,596, in the Journal of Catalysis, 22, 245-254 (1971) and in German Offenlegungsschrift No. 4,138,141, for example. Other catalysts, comprising nickel, cobalt and copper on zeolites, have been shown to reduce the chlorine content in carbon tetrachloride, forming chloroform and 1,1,1-tetrachloroethane in the Journal of Catalysis, 34, 136-143 (1982).

SUMMARY OF THE INVENTION

The present invention relates to the catalytic hydrodechlorination of chloromethane compounds, including carbon tetrachloride and the chlorofluoromethane compounds, by treatment with hydrogen in the presence of a transition metal carbide catalyst, preferably supported on an oxidic support which also may contain a passivating layer of a ceramic between the support and catalyst. Tungsten carbide is a preferred catalyst, silicon carbide is a preferred passivating layer, and alumina is a preferred oxidic support. The term "carbide" as used herein is intended to cover carbide catalysts which also contain oxygen so as to be classified as "oxycarbides". Mixtures of distinct oxycarbide and carbide catalytic phases in the catalyst are also contemplated hereunder.

DESCRIPTION OF PREFERRED EMBODIMENTS

The catalytic hydrodechlorination process of the present invention can be used to remove chlorine (in the form of hydrogen chloride) from a chloromethane compound including carbon tetrachloride, which contains only chlorine, or a chlorofluoromethane, such as dichlorodifluoromethane or monochlorodifluoromethane. Thus, it is possible to convert the environmentally unacceptable dichlorodifluoromethane to the more acceptable chlorodifluoromethane and/or difluoromethane species.

The chlorine-containing methane which is to be hydrode-chlorinated is treated with hydrogen, preferably at elevated temperature (100° C. to 500° C.) and atmospheric pressure in the presence of a transition metal carbide catalyst, for example, at from about 1 mole to about 10 moles per one mole of the chloromethane which is to be reacted. The reaction can also be run under pressure with the use of correspondingly lowered temperatures. Both gas phase and liquid phase reaction media are contemplated for use.

The transition metal carbide catalyst suitable for use herein can be a carbide of a metal from Groups VB to VIIIB of the Periodic Table, preferably Group VIB such as molybdenum or tungsten or a mixture of a transition metal from Groups VB to Group VIIIB. Tungsten carbide is preferred. The surface area should be no less than about 1 m$^2$/gm, preferably from about 50 m$^2$/gm to about 600 m$^2$/gm.

In preferred embodiments the catalyst is supported on an oxidic support, such as silica, alumina, alumina-silica, titania, magnesia-alumina-silica, cordierite, or a zeolite, preferably in the form of an anhydrous, high surface area material. Most preferably, a passivating layer of a non-catalytic ceramic, such as silicon carbide or silicon nitride, is formed on the oxidic support (e.g., by pyrolysis of a precursor for such ceramic, such as a polycarbosilane, previously coated on the support). This passivating layer is deemed to prevent undesired interaction of the support with the catalyst thereon and/or to prevent undesired side reactions from occurring.

The carbide catalyst can be formed on the support or, preferably, passivated oxide support by first reacting a transition metal salt, such as a chloride, with an acyclic compound containing carbon-nitrogen-hydrogen bonding (e.g., guanidine, cyanamide, dicyanimide, or dicyandiamide) and then pyrolyzing the resulting composition as more fully described in U.S. Ser. No. 878,726, filed May 4, 1992, which is incorporated herein in its entirety.

The present invention is further illustrated by the Examples which follow.

EXAMPLE 1

Boehmite alumina was extruded into 1/32 inch cylinders and calcined at 950° C. This alumina was used as the support for Examples 2–4. Its surface area was 155 $m^2/gm$ and its pore volume was 0.72 cc/gm.

EXAMPLE 2

In this Example an alumina support was coated with a protective layer of silicon carbide.

Alumina extrudates (100 gm) from Example 1 was mixed with 100 gm of a solution made by dissolving 15 gm of polycarbosilane (from Nippon Carbon Company, Ltd.) in, 85 gm of heptane. The polycarbosilane solution was just enough to completely wet the alumina. The wet alumina extrudates were dried at 150° C. for thirty minutes and were then calcined under nitrogen at 1100° C. for two hours. Upon cooling, the extrudates appeared black throughout. The weight of the product was 28.3 gm. The calculated weight for alumina plus silicon carbide was 28.2 gm.

EXAMPLE 3

In this Example, the silicon carbide-coated alumina from Example 2 was coated with a second coating of tungsten carbide to form the composition of the present invention.

One hundred forty grams of the product prepared according to Example 2 was admixed with 120 gm of tungsten hexachloride and 86 gm of guanidine hydrochloride and heated at about 350° C. in a round bottom flask with mixing until most of the hydrogen chloride was evolved and white fumes of ammonium chloride started to appear. The material was then calcined at 775° C. for two hours under nitrogen. The XRD showed that the catalyst contains $W_2(C,O)$. Surface area by BET method showed 140 $m^2/gm$.

EXAMPLE 4

This Example demonstrates the catalytic activity of the composition described in Example 3. A gas stream of Freon-12 flowing at a rate of 20 cc/min was mixed with a stream of hydrogen gas flowing at a rate of 20 cc/min and the mixture was passed over 3 gm of the tungsten carbide supported on SiC-coated alumina. The catalyst temperature was maintained at 350° C. The conversion of dichlorodifluoromethane ($CCl_2F_2$) and selectivity to monochlorodifluoromethane ($CHClF_2$) were determined by gas chromatography (GC) peak areas, that were identified with pure gases prior to running the experiment. The gas composition was then changed to evaluate the effect of the ratio of hydrogen to Freon-12 on conversion. The catalyst was kept at temperature throughout the experiment which lasted 8.5 hours. The results are shown in the following Table:

| Hydrogen/$CCl_2F_2$ Feed ratio | Run Time Hours | % Conversion of $CCl_2F_2$ | % Selectivity to $CHClF_2$ |
| --- | --- | --- | --- |
| 1/1 | 2 | 16.4 | 67.3 |
| 1/2 | 5 | 19.2 | 86.1 |
| 1/3 | 7 | 19.6 | 91.8 |
| 1/4 | 8.5 | 18.1 | 95.1 |

The best results were obtained at ¼ hydrogen to $CCl_2F_2$ ratio, where selectivity to $CHClF_2$ in the highest at 95.1%. It is also clear the gas composition did not affect much the conversion of $CCl_2F_2$.

EXAMPLE 5

This Example shows the effect of temperature on performance. After the elapse of 8.5 hours on stream from the above Example, the gas mixture composition was maintained at ¼ hydrogen to dichlorodifluoromethane and the temperature was increased to 400 and 450° C. successively and the effluent gas was analyzed by GC at each temperature. The time elapsed since exposing the catalyst in Example 1 was recorded in order to briefly check the stability of the catalyst. The results are shown in the following Table:

| Reaction Temperature (°C.) | Run Time Hours | % Conversion of $CCl_2F_2$ | % Selectivity to $CHClF_2$ |
| --- | --- | --- | --- |
| 400 | 11 | 56.1 | 93.7 |
| 450 | 12 | 76.1 | 95.1 |

It is apparent that increasing the temperature increased the conversion of dichlorodifluoromethane, while has no effect on selectivity. Limitations on the design of a commercial catalytic converter will determine the optimum conditions, i.e. the highest conversion with the highest selectivity.

EXAMPLE 6

This Example illustrates the catalytic conversion of monochlorodifluorocarbon ($CHClF_2$) to the completely fluorinated and more environmentally safe difluoromethane ($CH_2F_2$).

The catalyst was prepared by impregnating 35 gm of a zeolite with a solution containing 8.6 gm of guanidine hydrochloride, 12 gm of tungsten chloride and 100 cc cold ethanol, followed by drying at 150° C. for three hours, 450° C. for two hours and 750° C. for two hours. Two grams of the catalyst were placed in a tubular reactor, heated to different temperatures, and treated with a mixture of a gas containing $CHClF_2$ flowing at a rate of 8 cc/min and hydrogen at 32 cc/min. The product gas was analyzed by gas chromatography. The results are given in the following Table:

| Reaction Temperature (°C.) | Run Time Hours | Conversion of $CHClF_2$, % | Selectivity to $CH_2F_2$, % |
| --- | --- | --- | --- |
| 350 | 1.7 | 15 | 79 |
| 400 | 2.1 | 39 | 75 |
| 450 | 2.9 | 93 | 82 |

The results show the high conversion and high selectivity of the catalyst at 450° C.

EXAMPLE 7

This Example describes the catalytic conversion of carbon tetrachloride by a tungsten carbide catalyst supported on alumina, with a surface area of 160 $m^2/g$ and pore volume of 0.47 cc/g. Liquid carbon tetrachloride was fed by a pump at a rate of 0.005 cc/min into a catalytic reactor containing 1 gm of catalyst. The reactor was heated at different temperatures, together with a stream of hydrogen gas at a flow rate of 20 cc/min. The product were analyzed with a gas chromatograph. The results are given in the following Table:

| Reaction Temperature (°C.) | CCl$_4$ Conversion (%) | Selectivity % | | |
|---|---|---|---|---|
| | | CHCl$_3$ | Hydrocarbons | Cl$_3$C.CH$_2$Cl |
| 200 | 10 | 30 | 0 | 70 |
| 240 | 30 | 20 | 0 | 75 |
| 300 | 100 | 5 | 10 | 70 |
| 350 | 100 | 0 | 30 | 45 |
| 500 | 100 | 0 | 100 | 0 |

This Example shows that the conversion of carbon tetrachloride to useful products such as chloroform and 1,1,1,2 tetrachloroethane, two precursors to harmless fluorocarbons took place at low temperatures of 200°–350° C. At higher temperature of 500° C., conversion to hydrocarbons and HCl. This temperature is much lower than the 1500° C. temperature needed to decompose undesirable chemical waste containing halocarbons by incineration.

The foregoing Examples are presented for illustrative purposes only and, for that reason, should not be construed in a limiting sense. The scope of protection sought is set forth in the claims which follow.

I claim:

1. A process for the catalytic hydrodechlorination of a chloromethane which comprises treating the chloromethane with hydrogen at elevated temperature in the presence of a transition meal carbide catalyst, supported on an oxidic support with a ceramic passivating layer lying between the support and the catalyst to remove chlorine from the chloromethane compound in the form of hydrogen chloride.

2. A process as claimed in claim 1 wherein the chloromethane is selected from the group consisting of carbon tetrachloride and the chlorofluoromethanes.

3. A process as claimed in claim 1 wherein the transition metal is tungsten.

4. A process as claimed in claim 1 wherein the chloromethane is dichlorodifluoromethane and the transition metal is tungsten.

5. A process as claimed in claim 1 wherein the transition metal in the catalyst is a Group VIB element and the catalyst, which has a surface area of no less than about 1 m$^2$/gm, is supported on an oxidic support.

6. A process as claimed in claim 5 wherein the metal is tungsten.

7. A process as claimed in claim 1 wherein the chloromethane is dichlorodifluoromethane and the catalyst is tungsten carbide which is supported on the oxidic support.

8. A process as claimed in claim 7 wherein the support is alumina.

9. A process as claimed in claim 7 wherein the support is alumina and the passivating layer is silicon carbide.

10. A process as claimed in claim 7 wherein the support is a zeolite.

* * * * *